United States Patent
Pimenta et al.

(10) Patent No.: US 9,144,501 B1
(45) Date of Patent: Sep. 29, 2015

(54) FRACTURE REDUCTION DEVICE AND METHODS

(75) Inventors: Luiz Pimenta, São Paulo (BR); Lukas Eisermann, San Diego, CA (US); Matthew Copp, San Diego, CA (US); Nicholas Phillips, Laguna Niguel, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 13/184,576

(22) Filed: Jul. 18, 2011

Related U.S. Application Data

(60) Provisional application No. 61/365,122, filed on Jul. 16, 2010, provisional application No. 61/365,108, filed on Jul. 16, 2010.

(51) Int. Cl.
*A61F 2/44* (2006.01)

(52) U.S. Cl.
CPC . *A61F 2/44* (2013.01); *A61F 2/442* (2013.01); *A61F 2/447* (2013.01)

(58) Field of Classification Search
CPC .......... A61F 2/44; A61F 2/4455; A61F 2/447
USPC ............... 623/17.11–17.16; 403/109.1–109.8
See application file for complete search history.

(56) References Cited

U.S. PATENT DOCUMENTS

| | | | |
|---|---|---|---|
| 4,969,888 A | 11/1990 | Scholten et al. | |
| 5,827,289 A | 10/1998 | Reiley et al. | |
| 6,213,672 B1 * | 4/2001 | Varga | 403/109.2 |
| 6,241,734 B1 | 6/2001 | Scribner et al. | |
| 6,248,110 B1 | 6/2001 | Reiley et al. | |
| 6,280,456 B1 | 8/2001 | Scribner et al. | |
| 6,419,705 B1 * | 7/2002 | Erickson | 623/17.16 |
| 6,562,074 B2 | 5/2003 | Gerbec et al. | |
| 6,740,093 B2 | 5/2004 | Hochschuler et al. | |
| 6,852,129 B2 * | 2/2005 | Gerbec et al. | 623/17.15 |
| 6,863,673 B2 | 3/2005 | Gerbec et al. | |
| 6,981,981 B2 | 1/2006 | Reiley et al. | |
| 7,044,954 B2 | 5/2006 | Reiley et al. | |
| 7,114,501 B2 | 10/2006 | Johnson et al. | |
| 7,153,306 B2 | 12/2006 | Ralph et al. | |
| 7,166,121 B2 | 1/2007 | Reiley et al. | |
| 7,226,481 B2 | 6/2007 | Kuslich | |
| 7,241,303 B2 | 7/2007 | Reiss et al. | |
| 7,261,720 B2 | 8/2007 | Stevens et al. | |
| 7,500,992 B2 | 3/2009 | Li | |

(Continued)

FOREIGN PATENT DOCUMENTS

| | | |
|---|---|---|
| AU | 2002323730 B2 | 9/2004 |
| CN | 2730336 Y | 10/2005 |

(Continued)

*Primary Examiner* — Matthew Lawson
*Assistant Examiner* — Si Ming Lee
(74) *Attorney, Agent, or Firm* — Jonathan Spangler; Jennifer Russell

(57) ABSTRACT

A fracture reduction implant for treating a vertebral compression fracture and instruments and methods for implanting the fracture reduction device utilizing a minimally invasive lateral approach are described. The implant may be inserted into a fractured vertebra through a T-shaped cut formed in the vertebral wall. The T-shaped cut may be formed in the lateral aspect of the wall. After insertion, a portion of the implant may be elevated within the vertebral body to reduce the fracture. The implant may include a base assembly, elevator plate, and a support column. The support column may be locked to the base assembly after insertion.

6 Claims, 20 Drawing Sheets

(56) References Cited

U.S. PATENT DOCUMENTS

| | | |
|---|---|---|
| 7,615,052 B2 | 11/2009 | Serbousek |
| 7,621,952 B2 | 11/2009 | Truckai et al. |
| 7,623,902 B2 | 11/2009 | Pacheco |
| 7,666,227 B2 | 2/2010 | Schaller |
| 7,682,364 B2 | 3/2010 | Reiley et al. |
| 7,682,378 B2 | 3/2010 | Truckai et al. |
| 7,708,733 B2 | 5/2010 | Sanders et al. |
| 7,713,273 B2 | 5/2010 | Krueger et al. |
| 7,744,637 B2 | 6/2010 | Johnson et al. |
| 7,749,255 B2 | 7/2010 | Johnson et al. |
| 7,758,644 B2 | 7/2010 | Trieu |
| 7,780,734 B2 | 8/2010 | Johnson et al. |
| 7,789,912 B2 | 9/2010 | Manzi et al. |
| 7,803,188 B2 | 9/2010 | Justis et al. |
| 7,811,291 B2 | 10/2010 | Liu et al. |
| 7,875,078 B2 | 1/2011 | Wysocki et al. |
| 7,901,409 B2 | 3/2011 | Canaveral et al. |
| 7,909,873 B2 | 3/2011 | Tan-Malecki et al. |
| 7,955,339 B2 | 6/2011 | Schwardt et al. |
| 7,959,638 B2 | 6/2011 | Osorio et al. |
| 7,967,827 B2 | 6/2011 | Osorio et al. |
| 7,967,867 B2 | 6/2011 | Barreiro et al. |
| 7,972,340 B2 | 7/2011 | Sand et al. |
| 7,972,382 B2 | 7/2011 | Foley et al. |
| 7,985,228 B2 | 7/2011 | Phan et al. |
| 8,034,071 B2 | 10/2011 | Scribner et al. |
| 8,048,030 B2 | 11/2011 | McGuckin, Jr. et al. |
| 8,052,661 B2 | 11/2011 | McGuckin, Jr. et al. |
| 8,070,754 B2 | 12/2011 | Fabian et al. |
| 8,109,933 B2 | 2/2012 | Truckai et al. |
| 8,114,084 B2 | 2/2012 | Betts |
| 8,123,755 B2 | 2/2012 | Johnson et al. |
| 2003/0050644 A1 | 3/2003 | Boucher et al. |
| 2003/0130664 A1 | 7/2003 | Boucher et al. |
| 2003/0171812 A1 | 9/2003 | Grunberg et al. |
| 2004/0087947 A1 | 5/2004 | Lim et al. |
| 2005/0119662 A1 | 6/2005 | Reiley et al. |
| 2005/0278036 A1 | 12/2005 | Leonard et al. |
| 2005/0288678 A1 | 12/2005 | Reiley et al. |
| 2006/0095138 A1 | 5/2006 | Truckai et al. |
| 2006/0122701 A1 | 6/2006 | Kiester |
| 2006/0129244 A1 | 6/2006 | Ensign |
| 2006/0155296 A1 | 7/2006 | Richter |
| 2006/0264967 A1 | 11/2006 | Ferreyro et al. |
| 2007/0032791 A1 | 2/2007 | Greenhalgh |
| 2007/0050030 A1 | 3/2007 | Kim |
| 2007/0055259 A1 | 3/2007 | Norton et al. |
| 2007/0067034 A1 | 3/2007 | Chirico et al. |
| 2007/0093822 A1 | 4/2007 | Dutoit et al. |
| 2007/0162132 A1 | 7/2007 | Messerli |
| 2007/0179611 A1 | 8/2007 | DiPoto et al. |
| 2007/0255410 A1* | 11/2007 | Dickson et al. ............. 623/17.11 |
| 2008/0004705 A1* | 1/2008 | Rogeau et al. ............. 623/17.16 |
| 2008/0009877 A1 | 1/2008 | Sankaran et al. |
| 2008/0039948 A1* | 2/2008 | Biedermann et al. ...... 623/17.16 |
| 2008/0045966 A1 | 2/2008 | Buttermann et al. |
| 2008/0051825 A1 | 2/2008 | Reiley et al. |
| 2008/0058674 A1 | 3/2008 | Jansen et al. |
| 2008/0058826 A1 | 3/2008 | Scribner et al. |
| 2008/0058855 A1 | 3/2008 | Reiley et al. |
| 2008/0065190 A1 | 3/2008 | Osorio et al. |
| 2008/0086133 A1 | 4/2008 | Kuslich et al. |
| 2008/0177387 A1* | 7/2008 | Parimore et al. ............. 623/17.16 |
| 2008/0234687 A1 | 9/2008 | Schaller et al. |
| 2008/0249604 A1 | 10/2008 | Donovan et al. |
| 2008/0281364 A1 | 11/2008 | Chirico et al. |
| 2008/0294167 A1 | 11/2008 | Goldin et al. |
| 2008/0300598 A1 | 12/2008 | Barreiro et al. |
| 2009/0024217 A1 | 1/2009 | Levy et al. |
| 2009/0054934 A1 | 2/2009 | Beyar et al. |
| 2009/0076520 A1 | 3/2009 | Choi |
| 2009/0088788 A1 | 4/2009 | Mouw |
| 2009/0138043 A1 | 5/2009 | Kohm |
| 2009/0138086 A1 | 5/2009 | Dewey |
| 2009/0164016 A1 | 6/2009 | Georgy et al. |
| 2009/0204215 A1* | 8/2009 | McClintock et al. ...... 623/17.11 |
| 2009/0240334 A1 | 9/2009 | Richelsoph |
| 2009/0247664 A1 | 10/2009 | Truckai et al. |
| 2009/0276048 A1 | 11/2009 | Chirico et al. |
| 2009/0281627 A1 | 11/2009 | Petit |
| 2009/0299282 A1 | 12/2009 | Lau et al. |
| 2009/0299373 A1 | 12/2009 | Sisken |
| 2009/0299401 A1 | 12/2009 | Tilson et al. |
| 2009/0326538 A1 | 12/2009 | Sennett et al. |
| 2010/0023017 A1 | 1/2010 | Beyar et al. |
| 2010/0030216 A1 | 2/2010 | Arcenio |
| 2010/0030284 A1 | 2/2010 | Abt et al. |
| 2010/0036381 A1 | 2/2010 | Vanleeuwen et al. |
| 2010/0054075 A1 | 3/2010 | Valaie |
| 2010/0070049 A1 | 3/2010 | O'Donnell et al. |
| 2010/0082033 A1 | 4/2010 | Germain |
| 2010/0082036 A1 | 4/2010 | Reiley et al. |
| 2010/0082073 A1 | 4/2010 | Thramann |
| 2010/0087826 A1 | 4/2010 | Manzi et al. |
| 2010/0087828 A1 | 4/2010 | Krueger et al. |
| 2010/0100184 A1 | 4/2010 | Krueger et al. |
| 2010/0179656 A1 | 7/2010 | Theofilos et al. |
| 2010/0198225 A1 | 8/2010 | Thompson et al. |
| 2010/0217335 A1 | 8/2010 | Chirico et al. |
| 2010/0234866 A1 | 9/2010 | Arcenio et al. |
| 2010/0247478 A1 | 9/2010 | Clineff et al. |

FOREIGN PATENT DOCUMENTS

| | | |
|---|---|---|
| DE | 102008030690 A1 | 1/2010 |
| DE | 102009011561 A1 | 9/2010 |
| DE | 102009011566 A1 | 9/2010 |
| WO | WO-98-56301 A1 | 12/1998 |
| WO | WO-99-29246 A1 | 9/1999 |
| WO | WO-99-62416 A1 | 12/1999 |
| WO | WO-2007-002108 A2 | 1/2007 |
| WO | WO-2008-060277 A2 | 5/2008 |
| WO | WO-2008-097659 A2 | 8/2008 |
| WO | WO-2010-063111 A1 | 6/2010 |
| WO | WO-2010-100287 A1 | 9/2010 |

* cited by examiner

FRACTURE REDUCTION DEVICE AND METHODS

CROSS-REFERENCE TO RELATED APPLICATIONS

This application is a non-provisional patent application claiming the benefit of priority from U.S. Provisional Patent Application Ser. No. 61/365,122, filed on Jul. 16, 2010, (incorporated by reference in its entirety herein) and U.S. Provisional Patent Application Ser. No. 61/365,108, filed on Jul. 16, 2010, (incorporated by reference in its entirety herein).

FIELD

The present application describes implants, instruments, and methods for treating bone fractures of the human spine.

BACKGROUND

Vertebral compression fractures are crushing injuries to one or more vertebrae and are most commonly associated with osteoporosis. Bones weakened by osteoporosis can collapse and the resulting decrease in vertebral body height can lead to back pain, development of neurological conditions, or exacerbation of preexisting neurologic conditions. Trauma and metastatic cancer are also causes of vertebral compression fractures.

Non-surgical treatment for vertebral compression fractures includes short term bed rest, analgesics, calcium and vitamin D supplements, external bracing, and other conservative measures. If non-surgical treatment does not alleviate the painful symptoms of the fracture, surgical intervention may be required. Typical compression fracture patients are elderly and often do not tolerate open surgical procedures well. For these reasons, minimally invasive surgical techniques for treating these fractures have been developed. One such technique is percutaneous vertebroplasty which involves injecting bone cement under pressure into the fractured vertebra to provide stabilization. A second technique is balloon kyphoplasty which uses two balloons that are introduced into the vertebra to reduce the fracture. The balloons are then deflated and removed, and bone cement is placed in the void. While these techniques have seen an increase in popularity, neither consistently elevates the vertebral body end plates sufficiently to fully restore lost bone height for all indications. The present invention is directed at overcoming, or at least improving upon, the disadvantages of the prior art.

SUMMARY

This application describes an implant assembly and methods for restoring bone height after a vertebral compression fracture. The implant may be used in the cervical, thoracic, and lumbar spine. According to one embodiment, the implant assembly includes a base plate, an elevator plate, and a support column. One or more locking mechanisms may also be provided. The implant components are available in multiple lengths, widths, and heights to tailor to the size requirements of each fracture.

The implant is preferably composed of a surgical-grade metal material, including, but not necessarily limited to, titanium, stainless steel, and cobalt chrome. Alternatively, the implant may be composed of a carbon fiber reinforced plastic (CFRP), epoxy, polyester, vinyl ester, nylon, or poly-ether-ether-ketone (PEEK), and/or ceramic-reinforced PEEK, alone or in combination with a surgical-grade metal material.

When implanting within the lumbar and thoracic spine, access to the operative site is accomplished via a lateral approach. In the lumber spine, the approach is preferably a neurophysiology-guided transpsoas approach in the lumbar spine. This approach provides a large access window to permit introduction of a robust implant better suited for fully restoring the vertebral height while still achieving advantages of a minimally invasive approach such that it is generally well tolerated by elderly patients. According to one example, the neurophysiology guided trans-psoas approach to the lumbar spine is performed as follows. The skin is incised at the appropriate lateral location. Blunt finger dissection through the muscle layers allows safe access into the retroperitoneal space. The finger is used to guide an initial instrument to the surface of the psoas muscle through the retroperitoneal space. Once the initial instrument is safely guided to the surface of the psoas muscle, it is attached to a neurophysiologic monitoring system which is used to guide the direction of the approach away from nearby nerves. Using neurophysiologic guidance, the initial instrument is gently advanced through the psoas muscle. The neurophysiologic monitoring system confirms location of nerves near the distal end of the instrument. Fluoroscopy may be used simultaneously to assure correct targeting of the vertebral fracture. Once the instrument is docked on the target vertebra in the desired position, the position is secured with a k-wire. An operative corridor is thereafter created using a series of sequential dilators and a retractor assembly.

Following creation of the operative corridor, a cavity is created in the vertebral body to receive the implant. The cavity is upside down T-shaped and may be created using a single box T-shaped cutter, or, using separate horizontal and vertical cutters (among other options). Multiple tamp-sizers can be used to dilate the T-shaped cut to the appropriate size. As the T-shaped cut is formed, cancellous bone is impacted outwards toward the cortical bone. Once the cavity is formed an implant may be inserted. The implant may include a base assembly, elevator plate, and support column. An appropriate base plate and elevator plate are chosen based on the size requirements of the patient. The elevator plate is lowered onto the base plate over support struts on the base plate. This construct including the base plate and elevator plate is introduced into the surgical site. This may be accomplished using a guide rod. The implant is introduced or advanced all the way across the vertebral space and positioned so that there is a small overhang over the cortical, lateral aspects of the vertebral body to help stabilize the implant and prevent subsidence in the softer cancellous bone.

The elevator plate is raised from the base plate using multiple distraction shims. The use of multiple distraction shims includes, inserting a small shim which distracts the elevator plate a certain height, removing the small shim and then repeating this process with progressively larger shims until the desired height is reached. According to one example, the distractor shims are simply support column of lesser height than the final support column height required. Once the vertebral end plates are raised to the desired height, the final distraction shim is removed. The support column is inserted into the base plate-elevator plate assembly through a slotted passageway in the support struts. A restrictor pin affixed to the support struts may be provided to prevent disengagement of the elevator plate from the base. The support column is then locked to the base plate.

After implant placement, bone growth material may be used to fill the voids in the vertebra. Following successful implantation, the retractor assembly and all of the surgical instruments are removed and the operative corridor is closed.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The vertebral compression fracture reduction device and methods for use disclosed herein boasts a variety of inventive features and components that warrant patent protection, both individually and in combination.

Figure 1:
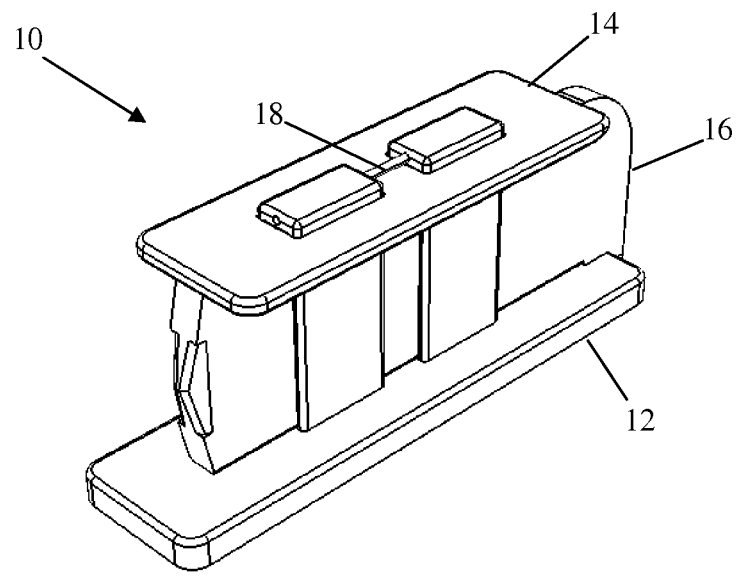
FIG. 1 is a perspective view of a fracture reduction implant assembly for treatment of a vertebral compression, according to one example embodiment.
Figure 2:
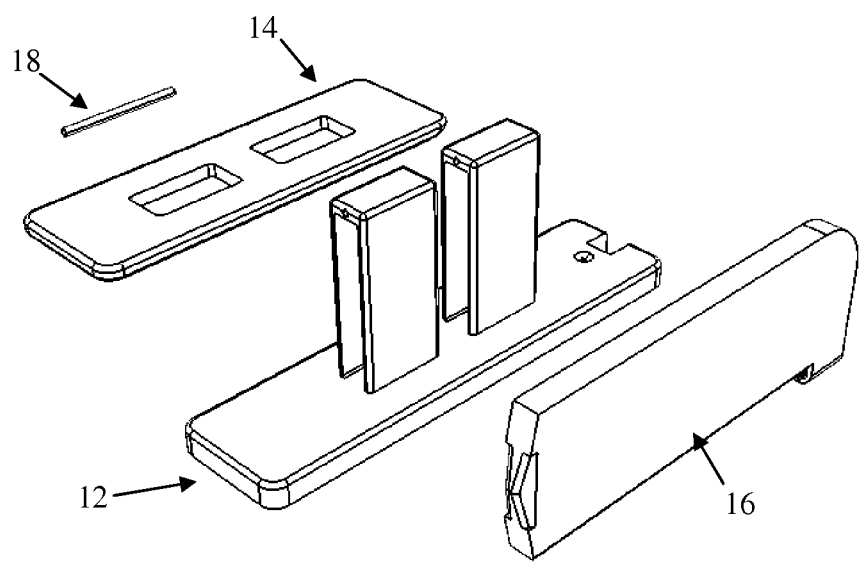
FIG. 2 is an exploded view of the implant assembly of FIG. 1.

FIGS. 1-2 illustrate one example embodiment of a fracture reduction implant 10 for treating a vertebral fracture. The implant 10 includes a base assembly 12, an elevator plate 14, and a support column 16. In use the implant 10 is inserted into a cavity formed in the fractured (target) vertebral body where it is expanded to restore the height of the vertebra and prevent recollapse in the future. The implant is optimized for insertion from a lateral access approach to the spine. The implant 10 may be used in any of the cervical, thoracic, and lumbar spine and may be sized accordingly.

Figure 3:
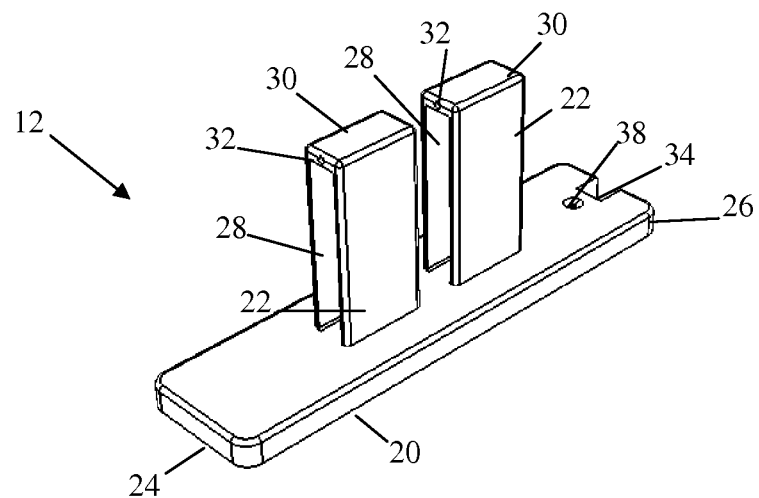
FIG. 3 is a perspective view of a base plate of the implant assembly of FIG. 1.

As illustrated in FIG. 3, the base assembly 12 includes a base plate 20 and a pair of support struts 22 extending generally perpendicularly from the base plate 20. It should be appreciated that while the present embodiment includes two support struts, a single support strut could be employed. It is also contemplated that more than two (e.g. 3, 4, 5, or 6) support struts could be employed. The base plate 20 has (by way of example) a generally rectangular footprint dimensioned to allow positioning across the vertebral body from a lateral insertion approach. The length of base plate 20 extends from a distal or leading end 24 to a proximal or trailing end 26. The length of the base plate 20 is preferably such that the base plate 20 spans the length of the vertebral body when inserted such that the proximal and distal ends 24, 26 extends to the cortical outer wall of the vertebral body, providing a solid base for the implant 10. By way of example, the base plate 20 length may be in the range of 45 mm to 60 mm. The base plate may have a width in the range of 14 mm to 26 mm. The height of the base assembly 12, including the base plate 20 and the support struts 22, may be in the range of 12 mm to 22 mm. According to one example, multiple base assemblies according to different size configurations are provided in order to match the implant 10 to the particular patient anatomy. By way of example, base assemblies may be provided with length dimensions increasing in 5 mm increments from 45 mm to 60 mm, width dimensions of 14 mm and 18 mm, and height dimensions increasing in 2 mm increments from 12 mm to 22 mm. The support struts 22 are centrally located on the base plate 20 and aligned one in front of the other such that there is a distal support strut and a proximal support strut. Each support strut 22 includes a slot 28 extending from the base plate 12 to an upper surface 30. The slot 28 is dimensioned to slidably receive the support column 16 therethrough. A pin channel 32 is provided in the upper surface 30 of each support strut 22. The pin channels 32 are aligned to slidably receive a restrictor pin 18 that prevents removal of the elevator plate 14 from the base assembly 12.

Figure 4:
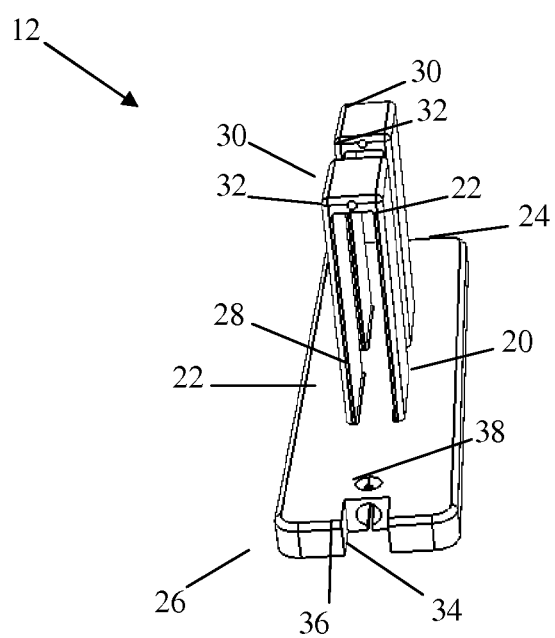
FIG. 4 is a perspective frontal view of the base plate of the implant assembly of FIG. 1.
Figure 18:
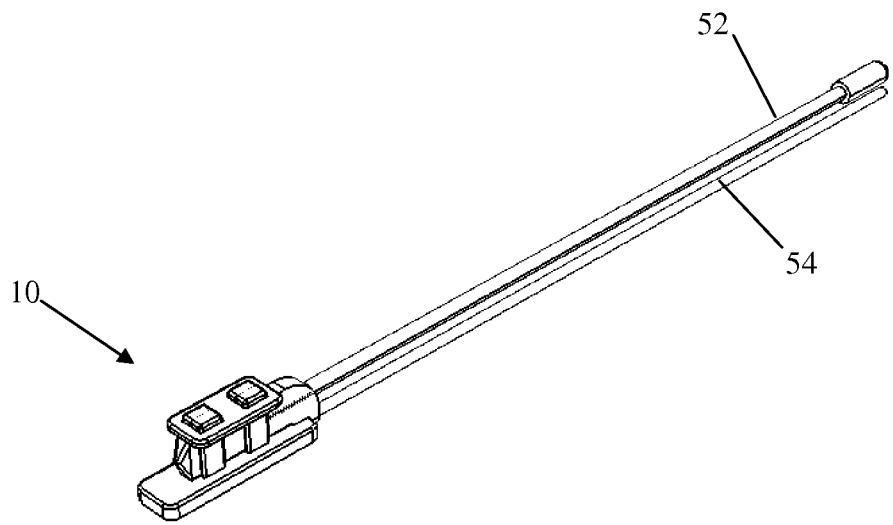
FIG. 18 is a perspective view of the base plate, elevator plate, and support column of the implant assembly of FIG. 1 with a guide rod and support column inserter coupled thereto.

FIG. 4 illustrates the proximal end 26 of base plate 20 which includes both a notch 34 and a dimple detent 38 for aligning and capturing support column 16. Within notch 34, a guide hole 36 is provided. The guide hole 36 is dimensioned to receive a guide rod 54 (FIGS. 18-19) which may be used to facilitate insertion of support column 16 along the appropriate path such that the support column 16 is easily passed through the slots 28 in the support struts 22.

Figure 5:
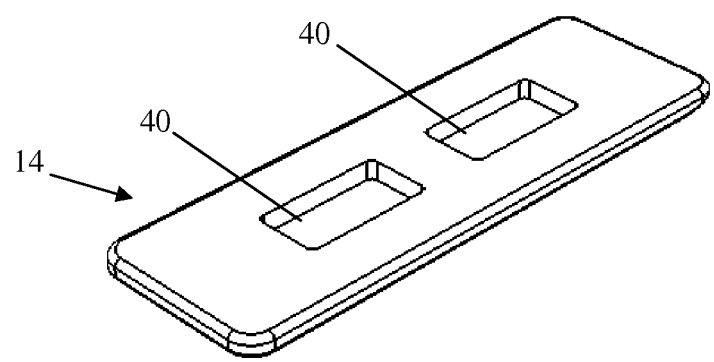
FIG. 5 is a perspective view of an elevator plate of the implant assembly of FIG. 1.

The elevator plate 14 has a rectangular shape like base plate 20, as illustrated in FIG. 5. According to this embodiment, the width of elevator plate 14 is shorter on either side of midline than the base plate 20. For example, the width of the elevator plate 14 may be 7.5 mm shorter on either side of midline than the base plate 20. It will be appreciated, however, that according to other embodiments the elevator plate 14 may have the same width or have a greater width than the base plate 20. The elevator plate 14 has two holes 40 for receiving the support struts 22. The holes 40 are arranged in the elevator plate 14 to align with the support struts 22 and are centrally located with one hole situated in front of the other such that there is a distal hole and a proximal hole.

Figure 6:
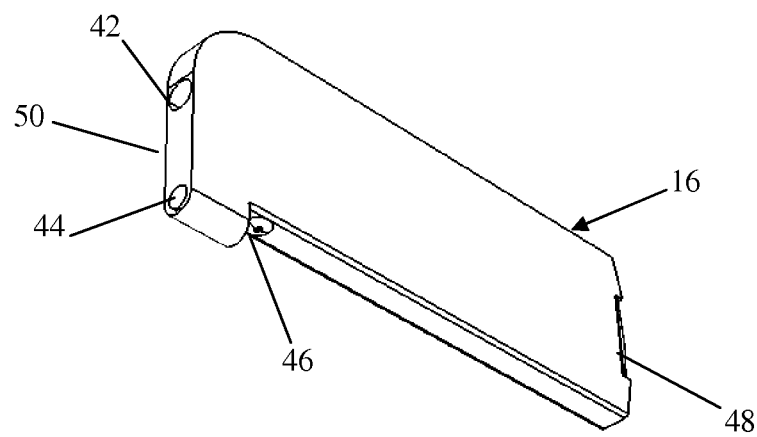
FIG. 6 is a perspective view of a support column of the implant assembly of FIG. 1.
Figure 19:
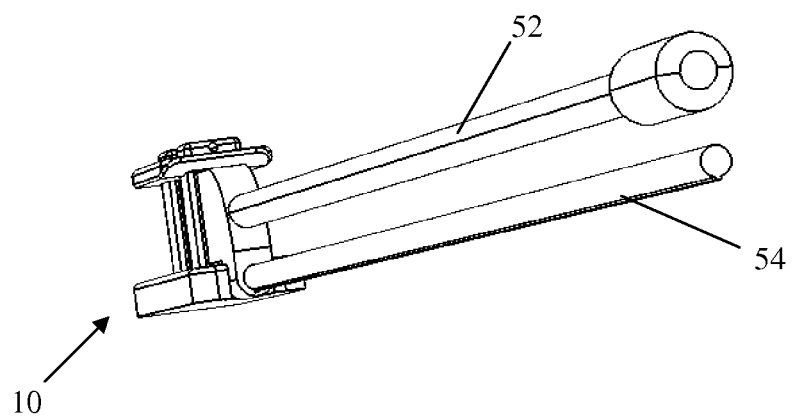
FIG. 19 is another perspective view showing the proximal ends of the base plate, elevator plate, and support column of the implant assembly of FIG. 1 with a guide rod and support column inserter coupled thereto.
Figure 20:
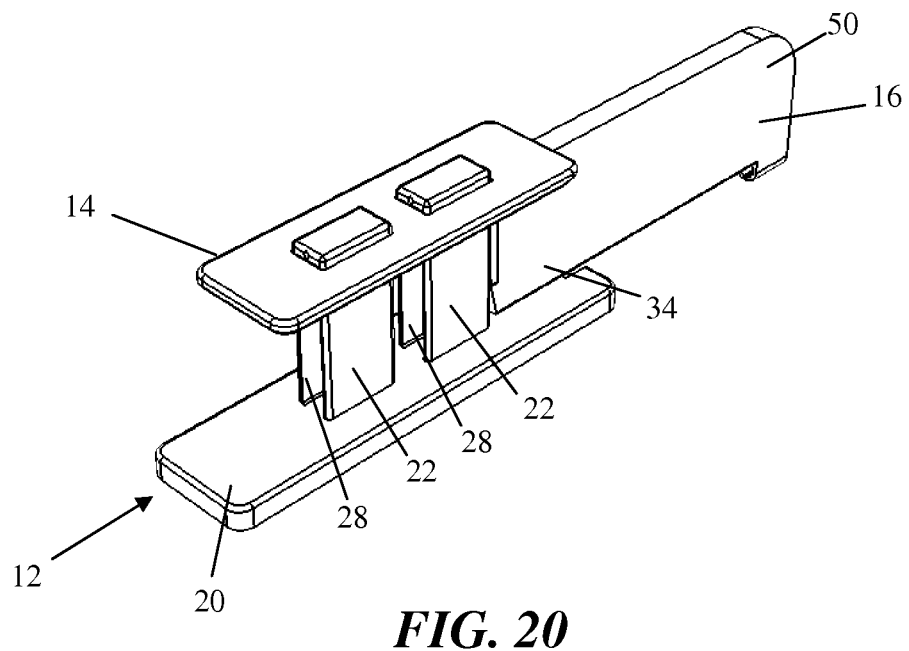
FIG. 20 is a perspective view showing the elevator plate of the implant assembly of FIG. 1 in the elevated position with the support column ready for insertion.

FIG. 6 illustrates the support column 16 and its features. The distal or leading end 48 of the support column 16 is dimensioned to facilitate insertion of support column 16 along the appropriate path such that the support column 16 is easily passed through the support slots 28 in the support struts 22. The proximal end 50 of the support column 16 contains an inserter rod hole 42 that couples with the inserter rod 52 (FIGS. 18-19), a guide rod aperture 44 that aligns with the guide hole 36 on the base plate 20 and is dimensioned to receive the guide rod 54 (FIGS. 19-20). On the inferior aspect of the support column 16, there is a ball 46 that is dimensioned to be complimentary to the dimple detent 24 of the base plate 20. Together, the ball 46 and dimple detent 24 provide a mechanism for securing the support column 16 to the base plate 20.

Figure 7:
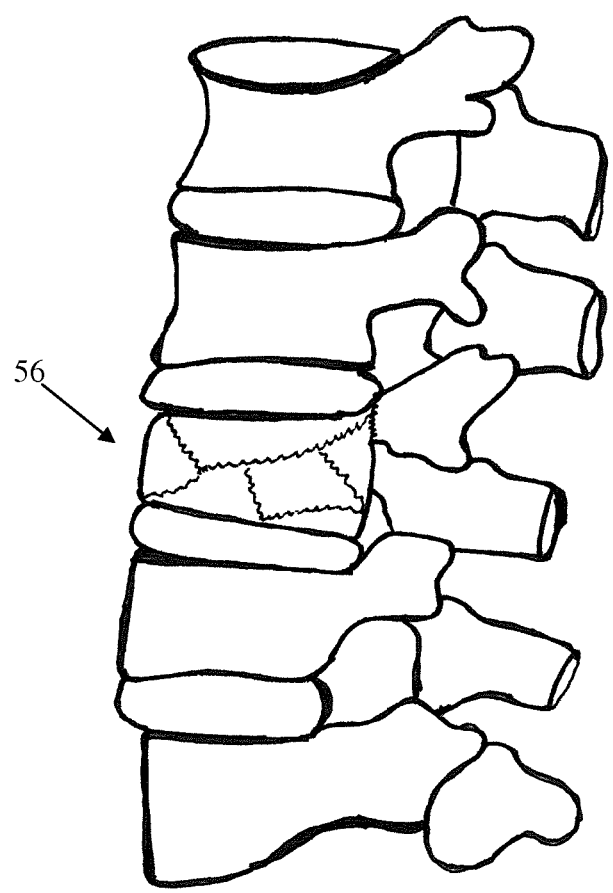
FIG. 7 is an illustration depicting a vertebral compression fracture that may be treated with the implant assembly of FIG. 1.
Figure 8:
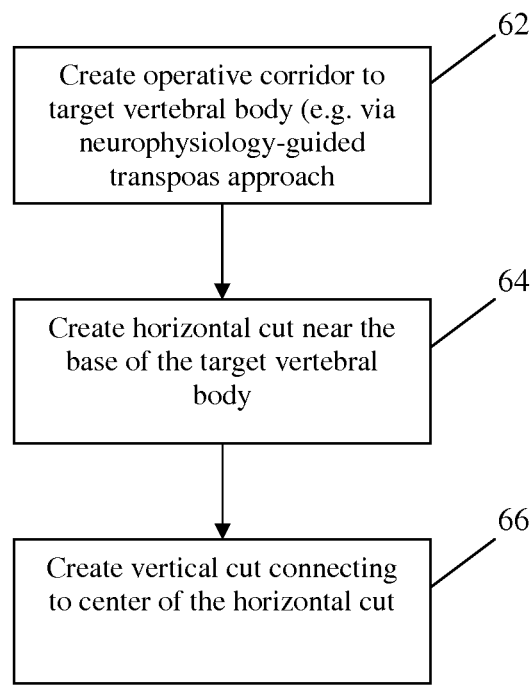
FIG. 8 is a flow chart outlining the steps according to one example method for preparing a target vertebral body for receiving the implant assembly of FIG. 1.
Figure 9:
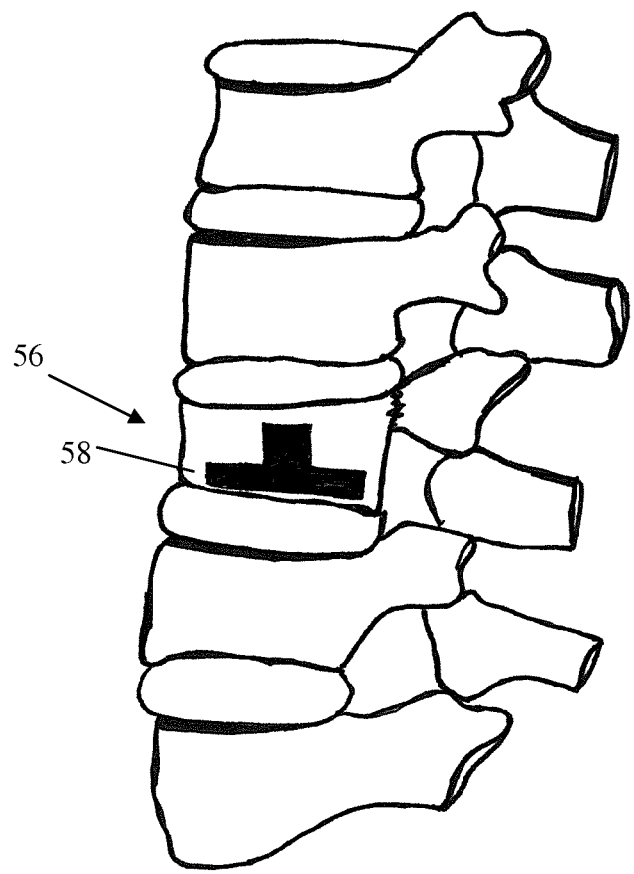
FIG. 9 is an illustration depicting the spine of FIG. 7 after preparing the target vertebral body according to the steps of FIG. 8.
Figure 10:
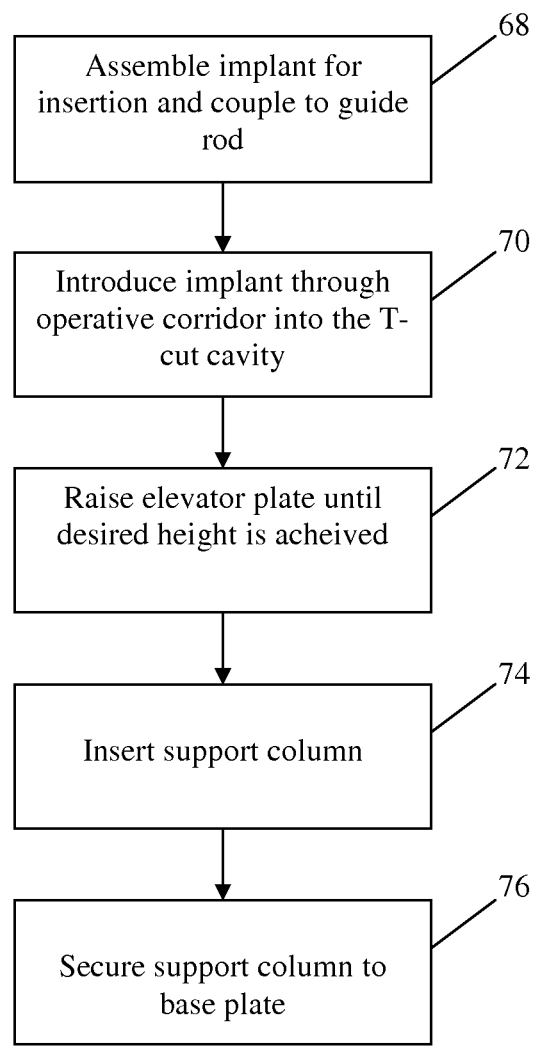
FIG. 10 is a flowchart outlining the steps according to one example method for implanting the implant assembly of FIG. 1 in order to reduce a vertebral compression fracture.

FIG. 7 is an illustration of a fractured vertebra 56 in the human patients spine for which the implant 10 may be deployed for treatment. FIG. 8 sets forth steps utilized according to one example method for preparing a target vertebra 56 within the spine to receive the implant 10. At step 62, and operative corridor to the vertebral body 56 is achieved via a lateral approach (e.g. a neurophysiology-guided transpsoas approach). At step 64, a first, horizontal cut is formed in the vertebral body 56 across the vertebral body from cortical wall to cortical wall. The first horizontal cut is sized to allow passage of the base plate 20 and elevator plate 14 (in the insertion position, i.e. with the elevator plate 14 resting on the base plate 20) into the cut. At step 66, a second, vertical cut is formed in the vertebral body 56. The vertical cut is sized to allow passage of the support struts 22 through the cut and connects with horizontal cut to form a (upside down) T-cut cavity. According to one example, a first horizontal cutter and a second vertical cutter, such as those shown and described in U.S. patent application Ser. No. 13/184,574, filed Jul. 18, 2011 (incorporated by reference herein), may be utilized to form the T-cut cavity. FIG. 9 illustrates the target vertebral body 56 after the T-cut 58 has been made. At this point, any remaining bony debris left inside the T-cut 58 may be removed using a small curette or other suitable surgical instrument.

Figure 11:
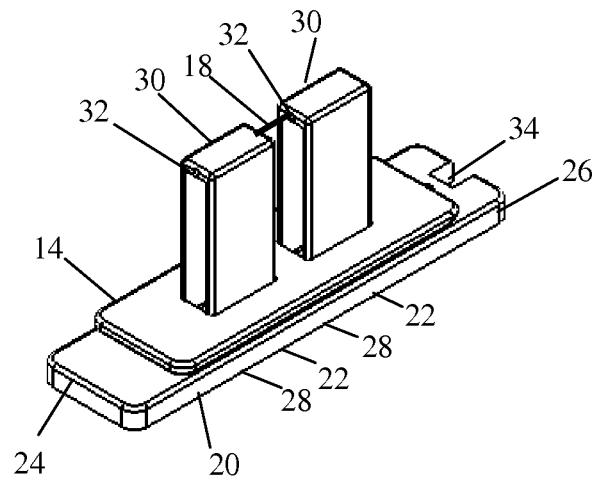
FIG. 11 is a perspective view of the base plate and elevator plate of the implant assembly of FIG. 1 in the insertion position with the elevator plate resting on the base plate.
Figure 12:
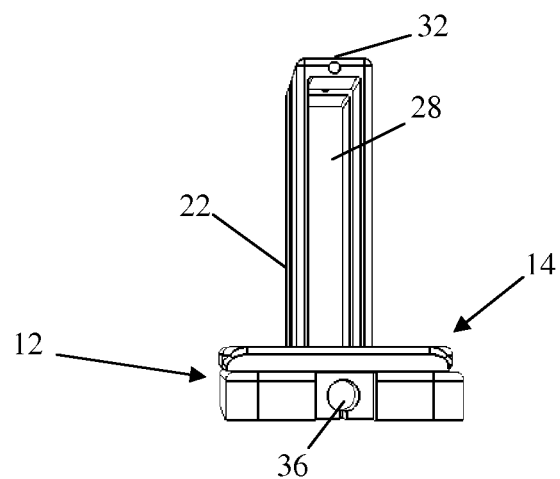
FIG. 12 is a proximal end view of the base plate and elevator plate of the implant assembly of FIG. 1 in the insertion position.
Figure 13:
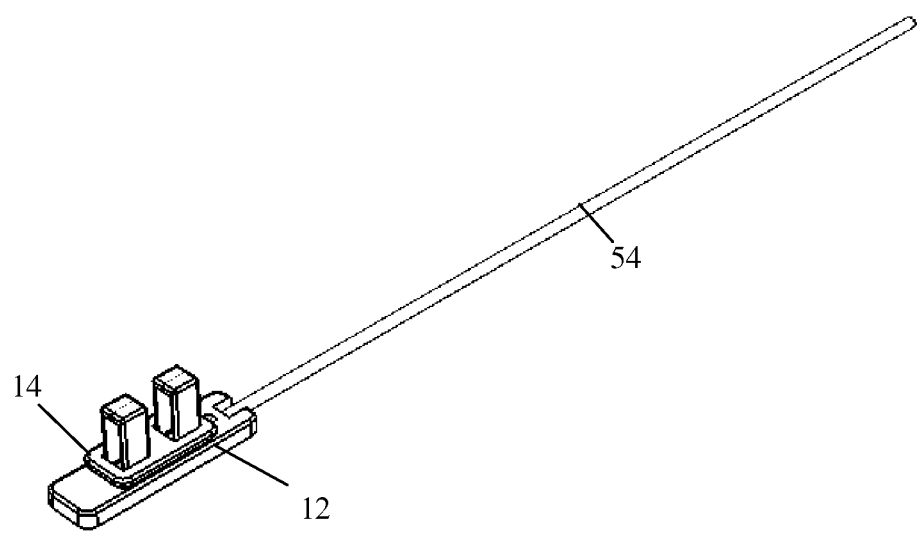
FIG. 13 is a perspective view of the base plate and elevator plate of the implant assembly of FIG. 1 in the closed position with an example embodiment of a guide rod attached to the base plate.
Figure 14:
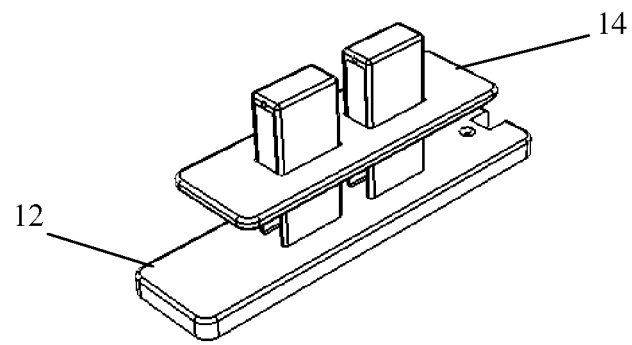
FIG. 14 is a perspective insertion view of the elevator plate of the implant assembly of FIG. 1 in a partially elevated position relative to the base plate.
Figure 15:
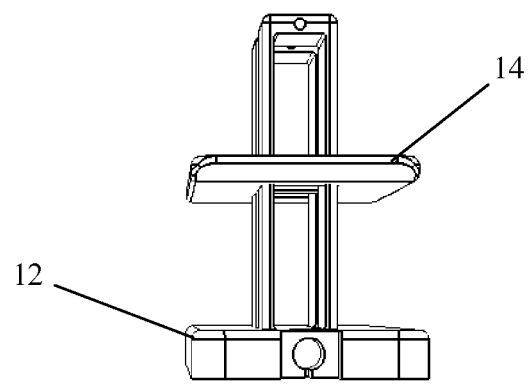
FIG. 15 is a proximal view of the elevator plate of the implant assembly of FIG. 1 in a partially elevated position relative to the base plate.

FIGS. 10-22 set forth and depict steps utilized according to one example method for deploying the implant into the target vertebral body 56. At step 68 the implant 10 is assembled (according to determined size requirements for the current patient anatomy) for insertion. That is, the holes 40 of the elevator plate 14 are aligned over the support struts 20 and advanced such that the elevator plate 14 rests on the base plate 20 in the insertion position (FIGS. 11-12). The restrictor pin 18 is placed within the pin channels 32 such that the elevator plate 14 is prevented from removal off the base assembly 12. Alternatively, it is possible that the restrictor pin 18, elevator plate 14, base plate 20 come preassembled. Also at step 68, a guide rod 54 (used to facilitate insertion and to later guide later insertion of the support column and distraction shims) is coupled to guide hole 36 on the base plate 20. With the implant 10 assembled in the insertion position and coupled to the guide rod 54, the assembly is advanced through the operative corridor and into the T-cut cavity 58 formed in the target vertebra such that the proximal and distal ends of the base plate 20 rest on the cortical bone of the outer wall.

Figure 16:
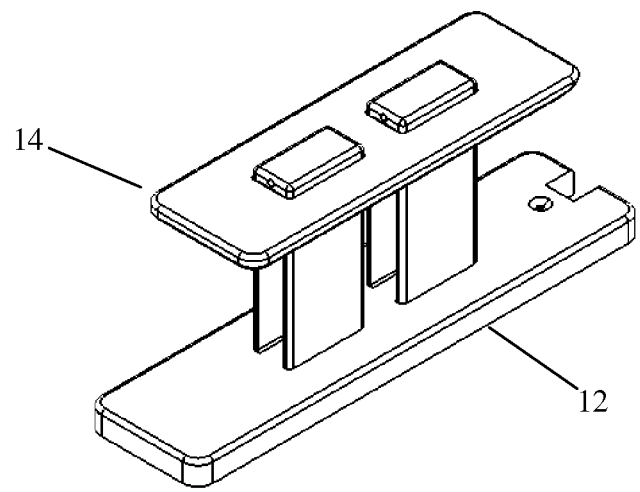
FIG. 16 is a perspective view of the elevator plate of the implant assembly of FIG. 1 in fully elevated position relative to the base plate.
Figure 17:
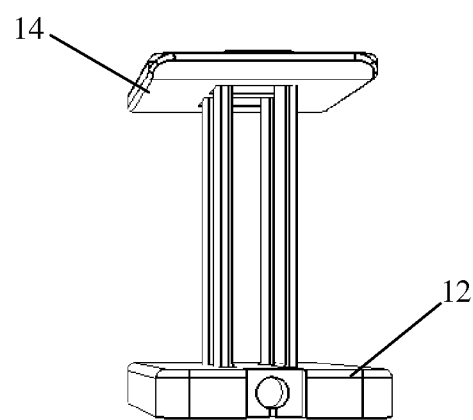
FIG. 17 is a proximal view of the elevator plate of the implant assembly of FIG. 1 in the fully elevated position relative to the base plate.

At step 72 the elevator plate is elevated to compress the cancellous bone in the interior of the vertebral body towards the cortical endplate, restoring the proper height of the vertebral body. To accomplish this, a series of sequentially larger distraction shims (not shown) are inserted between the elevator plate 14 and the base plate 20. The elevator plate 14 has a taped proximal end to facilitate receipt of the tapered distraction shims. Each of the sequentially larger distraction shims are inserted to incrementally raise the elevator plate (FIGS. 14-15) and then removed to make room for the next shim until the desired distraction height is achieved. Once the desired corrective height is achieved the last shim is removed to make room for the support column 16 (FIGS. 16-17). According to one example, the distraction shims are simply additional support columns (which are provided across a range of heights to accommodate the different implant heights and particular patient anatomy) of smaller height dimension than the final support column.

Figure 21:
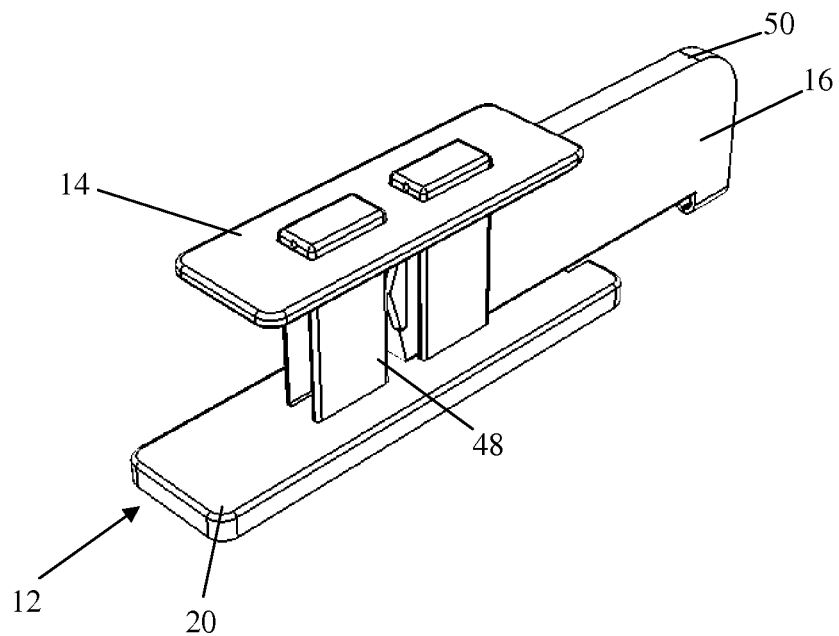
FIG. 21 is a perspective view showing the elevator plate of the implant assembly of FIG. 1 in the elevated position with the support column partially inserted.
Figure 22:
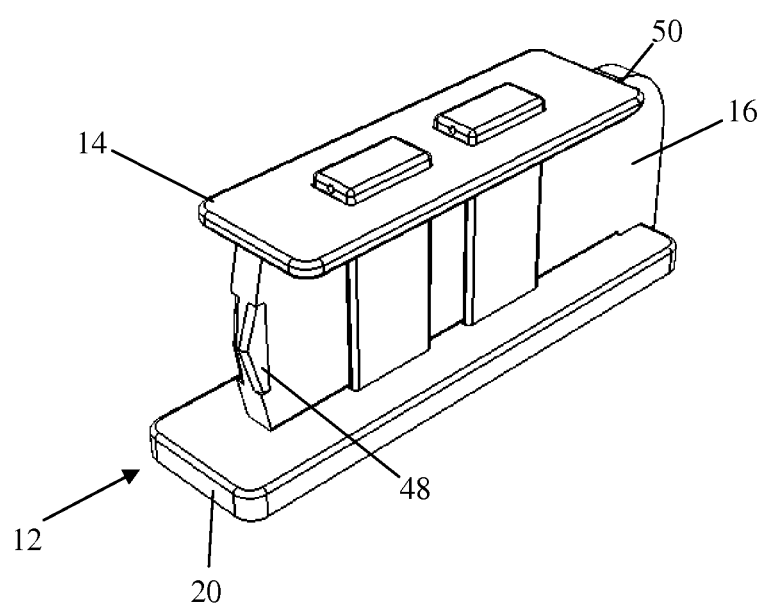
FIG. 22 is a perspective view showing the elevator plate of the implant assembly of FIG. 1, in the elevated position with the support column fully inserted.

At step 74, as highlighted in FIGS. 20-22, the support column 16 is advanced into the space formed between the elevator plate 14 and the base plate 20. To advance the support column 16, the inserter rod 52 is coupled to the proximal end 50 of the support column 16 at inserter hole 42. The guide hole 44 is inserted over the guide rod 54. Thus, the support column is advanced along the guide rod 54 to help align and pass the support column 16 through the slots 28 in the support struts 22. When the support column 16 is fully advanced through the support struts 22 (such that the fin through which the guide hole 44 passes rests within the notch 34 in the base plate 20), the ball 46 on the inferior surface of the support column 16 engages the detent 38 in the upper surface of the base plate to secure the support column 16 to the base plate 20 (step 76). Additional securing means may also be utilized to supplement or replace the ball detent. For example, a screw may be engaged through the support column guide hole 44 and into the guide hole 36 of the base plate 20 (after the guide rod 54 is removed), or by crimping the proximal (trailing) end 50 of the support column 20 to the proximal (trailing) end 26 of the base plate 20.

Figure 23:
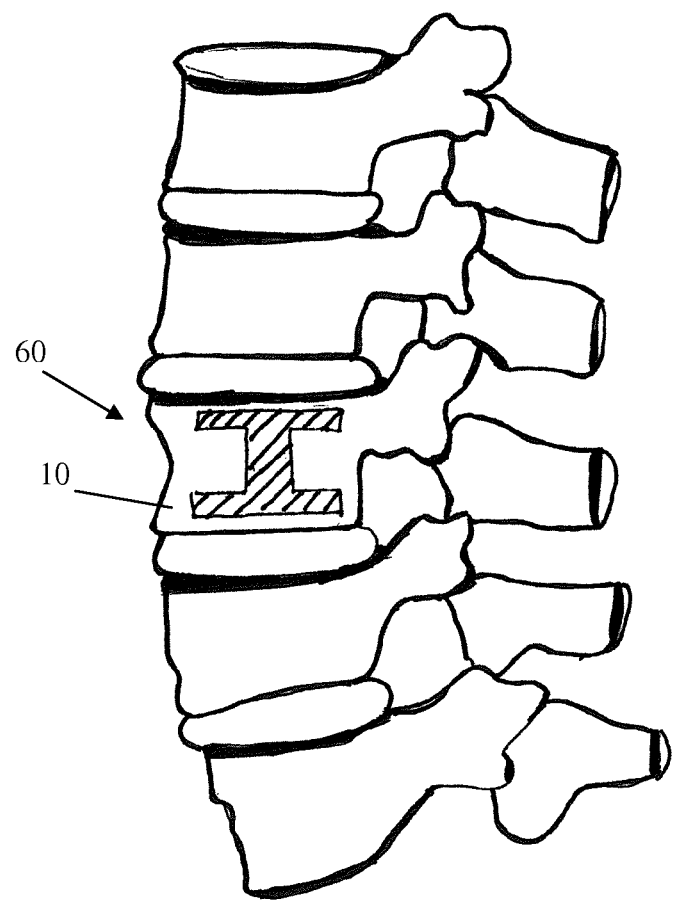
FIG. 23 is an illustration depicting the final implant configuration of the reduction implant assembly of FIG. 1 within the target vertebral body, following deployment of the implant assembly.

FIG. 23 shows the final implantation configuration of the implant 10 in a corrected (reduced) vertebra 60. It will be appreciated that the cancellous bone above the elevator plate 14 will be compressed toward the cortical endplate creating a void between the elevator plate and the base plate. The void may be filled with one or more of natural and synthetic bone growth materials and bone cement.

While not specifically described in detail above, it will be understood that various other steps may be performed in using and implanting the devices disclosed herein, including but not limited to creating an incision in a patient's skin, distracting and retracting tissue to establish the operative corridor to the surgical target site, advancing the implant through the operative corridor to the surgical target site, removing instrumentation from the operative corridor upon insertion of the implant, and closing the surgical wound.

The implant 10 and associated instruments and methods have been described above in terms of an example embodiment for achieving a vertebral body fracture reduction. It will be appreciated by those skilled in the art that various modifications and alternative forms may be employed without deviating from the spirit or scope of the invention. By way of example, FIGS. 24-32 illustrate a number of alternative example embodiments in which one or more modifications are made to the implant assembly 10. The embodiments illustrated in FIGS. 24-32 share many similar features with the implant 10 such that while modifications may be discussed below, repeat discussion of all features would be repetitive and unnecessary.

Figure 24:
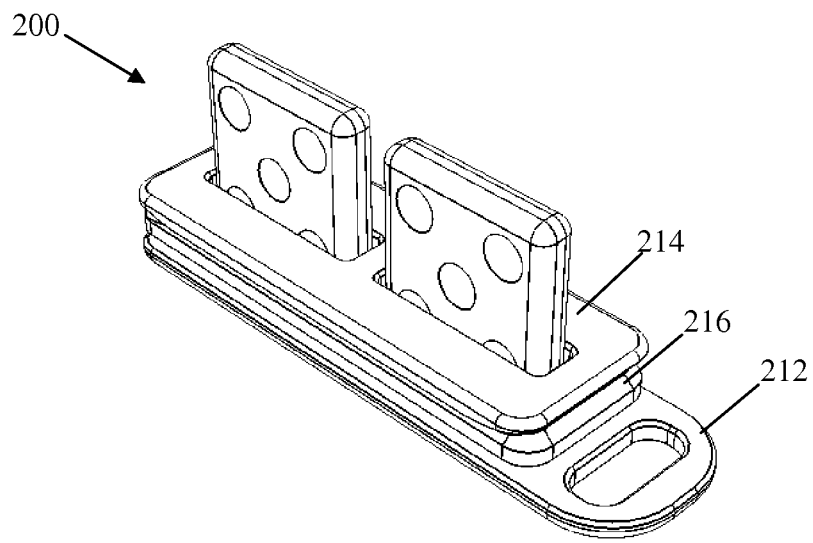
FIG. 24 is a perspective view of a fracture reduction implant assembly for treatment of a vertebral compression fracture, according to another example embodiment.
Figure 25:
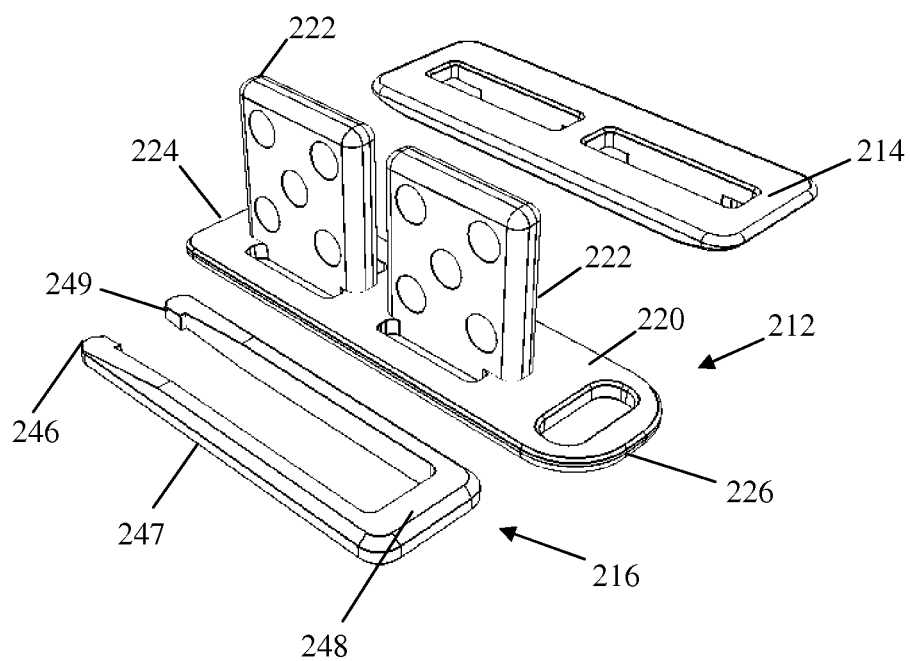
FIG. 25 is an exploded view of the implant assembly of FIG. 24.
Figure 26:
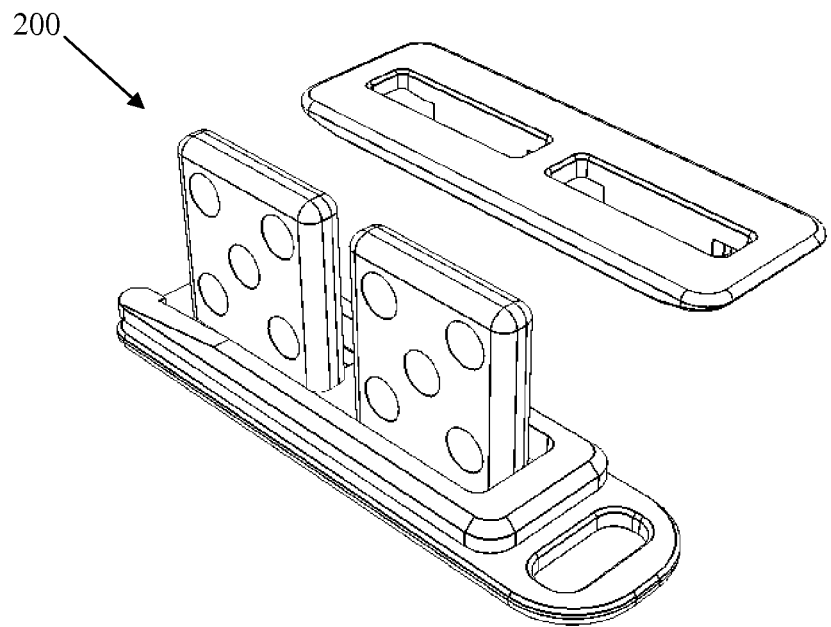
FIG. 26 is a perspective view of the implant assembly of FIG. 24 with the elevator plate removed.

FIGS. 24-26 illustrate an alternate example embodiment of a fracture reduction implant assembly 200. The implant 200 includes a base 212, an elevator plate 214, and a support column 216. The base 212 includes a base plate 220, extending from a proximal end 226 to a distal end 224, and a pair of fenestrated support struts 222, extending generally perpendicularly from the base plate 220. Unlike the support struts of the implant 10 the support struts 222 have no slot for passing the support column. Instead, the support column 216 is a U-shaped insert (best viewed in FIG. 25) with a closed proximal end 248 and an open distal end 246 separated by arms 247. As the support column 216 is inserted the arms pass along the exterior of the support struts 222, the arms 247 flex slightly during insertion due to flanges 247 at the distal end 246 which have an inward tapered leading edge. When the support column 216 is fully inserted the flanges 249 prevent unwanted removal of the support column. As described above, the distraction shims used to elevate the elevation plate and reduce the vertebral fracture may be support columns of lesser height (which are provided across a range of heights to accommodate the different implant heights and particular patient anatomy) than required for the final construct. In the embodiments shown in FIGS. 24-32 only the smallest heights are shown. Also in the embodiment of FIGS. 24-26

Figure 27:
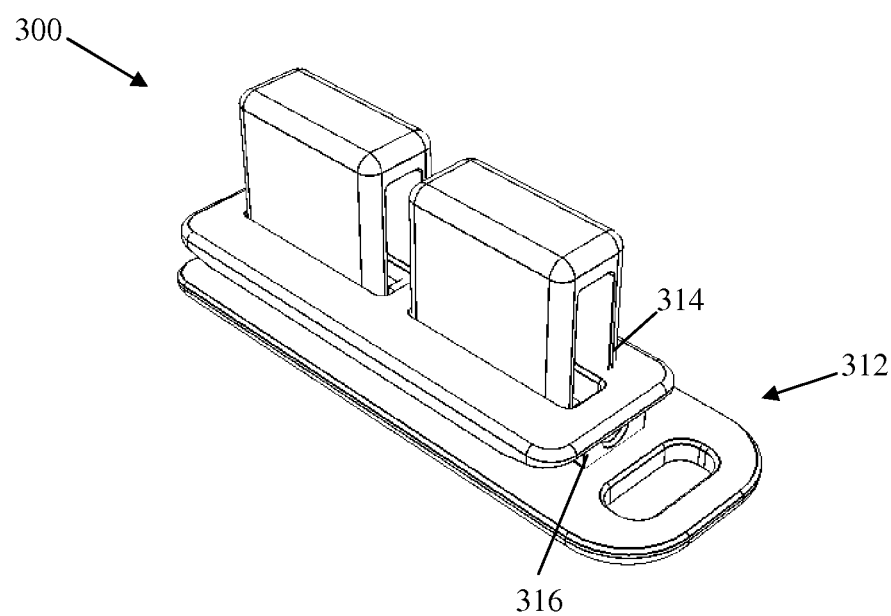
FIG. 27 is a perspective view of a fracture reduction implant assembly for treatment of a vertebral compression fracture, according to yet another example embodiment.
Figure 28:
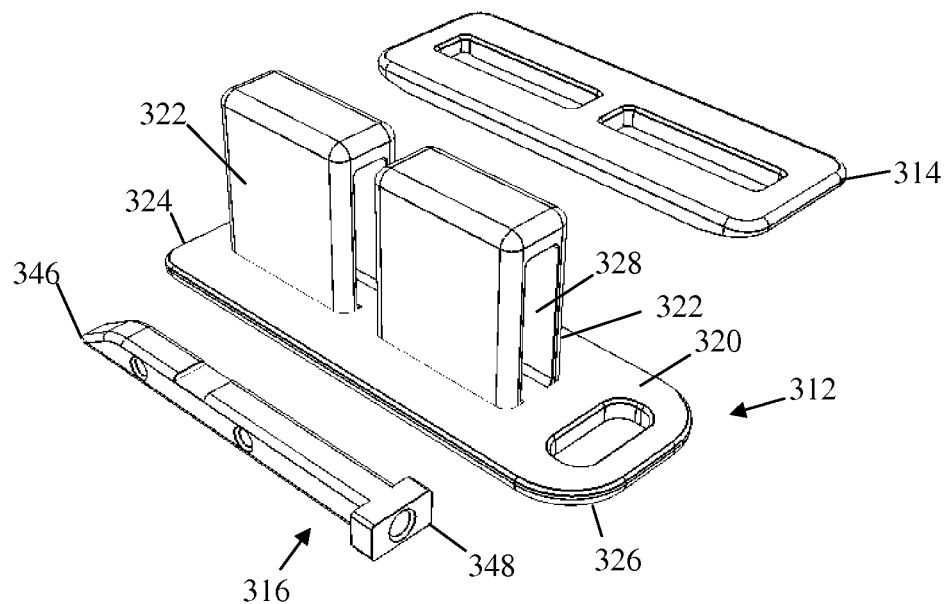
FIG. 28 is an exploded view of the implant assembly of FIG. 27.
Figure 29:
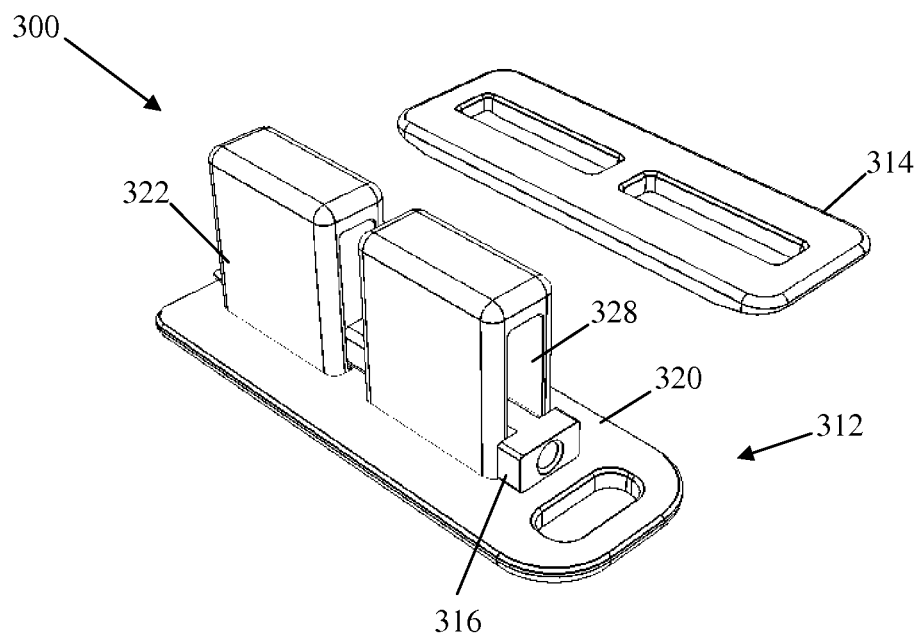
FIG. 29 is a perspective view of the implant assembly in FIG. 27 with the elevator plate removed.

FIGS. 27-29 illustrate another alternate example embodiment of a fracture reduction implant assembly 300. The implant 300 includes a base 312, an elevator plate 314, and a support column 316, as shown in FIG. 27. The base 312 includes a base plate 320, extending from a proximal end 326 to a distal end 324, and a pair of support struts 322 extending generally perpendicularly from the base plate 320 and having slot 328 formed therein. The support column 316 is shorter than the support column of the implant 10. Whereas the support column of the implant 10 extends the distance between the proximal support strut and the proximal end of the base plate (relying on engagement between the vertical fin and the base to stop advancement of the support column), the support column 316 does not extend the distance between the proximal support strut 322 and the proximal end of the base plate 320. Horizontal extensions of the support column proximal end 38 engage the support strut 322 to stop advancement of the support column.

Figure 30:
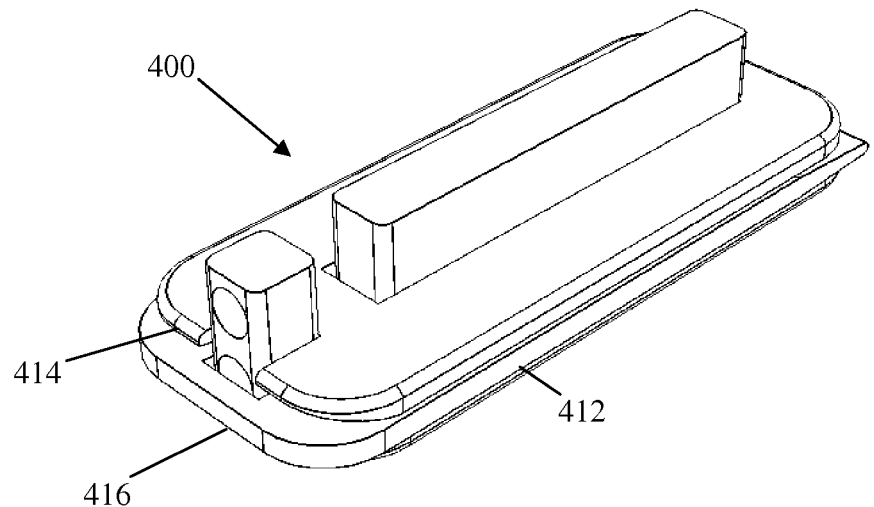
FIG. 30 is a perspective view of a fracture reduction implant assembly for treatment of a vertebral compression fracture, according to still one more example embodiment.
Figure 31:
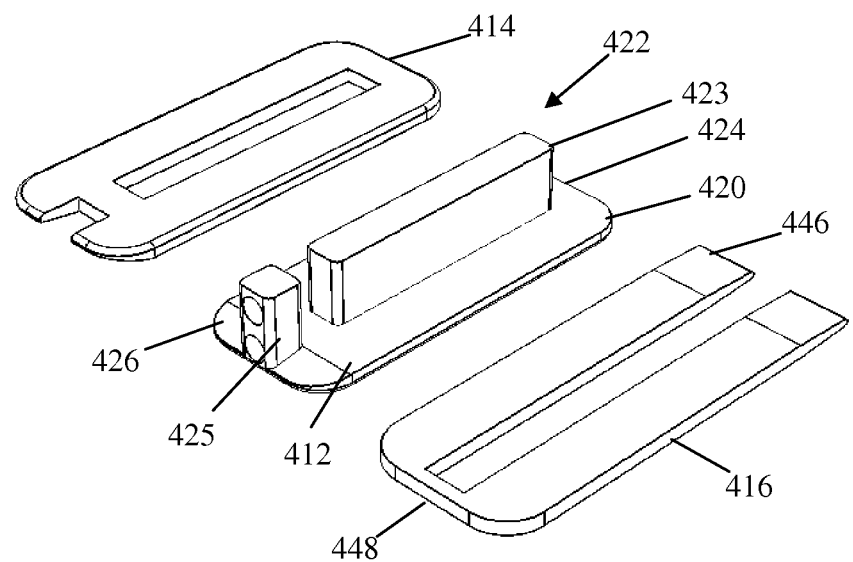
FIG. 31 is an exploded view of the implant assembly of FIG. 30.
Figure 32:
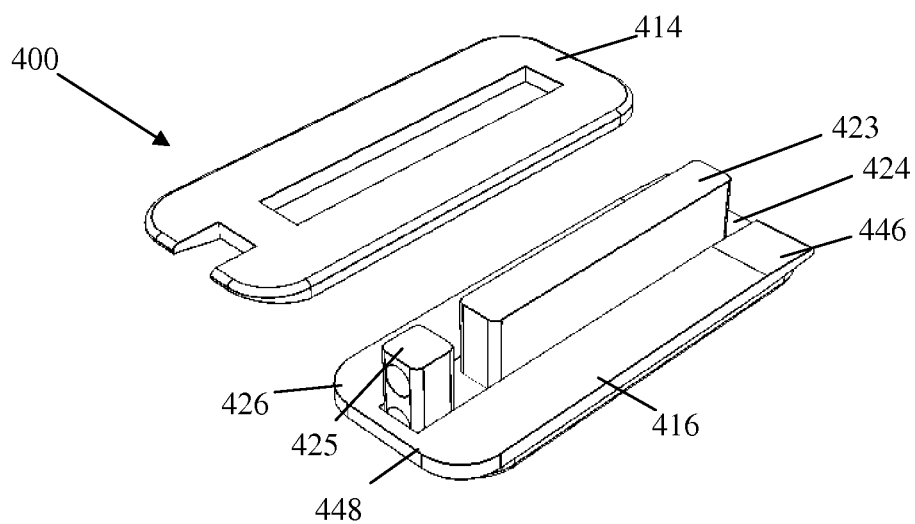
FIG. 32 is a perspective view of the implant assembly in FIG. 30 with the elevator plate removed.

FIGS. 30-32 illustrate another alternate example embodiment of a fracture reduction implant assembly 400. The implant 400 includes a base 412, an elevator plate 414, and a support column 416. The base 412 includes a base plate 420, extending from a proximal end 426 to a distal end 424, and a pair of support struts 422 extending generally perpendicularly from the base plate 420. The support struts 422 are asymmetrical and situated such that there is a long support strut 423 centered on the base plate 420 and a short support strut 425 proximal to the long support strut. The short support strut may sit flush with the proximal end 426 of the base plate. The support struts 422 are solid and have no slot for passing the support column. Instead, the support column 416 is a U-shaped insert (best viewed in FIG. 31) with a closed proximal end 448 and an open distal end 446 separated by arms 447 which straddle the support struts 422 when inserted.

While the invention is susceptible to various modifications and alternative forms, specific embodiments thereof have been described herein and shown drawings by way of example in the. It should be understood, however, that the description herein of specific embodiments is not intended to limit the invention to the particular forms disclosed, but on the contrary, the invention is to cover all modifications, equivalents and alternatives falling within the spirit and cope of the invention as defined by the e appended claims.

What is claimed is:

1. A fracture reduction device for reducing a compression fracture of a vertebral body, comprising:

a base having a rectangular shape with at least one support strut extending perpendicular to the base and configured so that the base and the at least one support strut together have an inverse T-shaped cross-section, said base having a length dimension that spans opposing lateral aspects of a vertebral body when inserted within said vertebral body and an overall width dimension;

an elevation platform having a bone contacting surface and an opposite interior surface and having at least one opening extending through the bone contacting surface and the interior surface of the elevation platform configured to receive therethrough the at least one support strut of the base when the base and the elevation platform are assembled together, said elevation platform having an overall width dimension that is less than the overall width dimension of the base; and a support column that is advanceable in a direction parallel to the length of the base between the base and the elevation platform and maintains the elevation platform in an elevated position above the base when positioned between the base and the elevation platform.

2. The fracture reduction device of claim 1, wherein the at least one support strut includes an elongate slot opening in proximal and distal faces of the at least one support strut.

3. The fracture reduction device of claim 2, wherein the support column is advanceable between the elongate slot opening of the at least one support strut.

4. The fracture reduction device of claim 1, wherein said support column and said base are secured together by a securing mechanism.

5. The fracture reduction device of claim 4, wherein said securing mechanism is a ball detent.

6. The fracture reduction device of claim 4, wherein said securing mechanism is a set screw that engages said base through a hole in said support column.

\* \* \* \* \*